United States Patent [19]

Lewis

[11] Patent Number: 4,904,928

[45] Date of Patent: Feb. 27, 1990

[54] MEASUREMENT APPARATUS AND METHOD UTILIZING MULTIPLE RESONANT MODES OF MICROWAVE ENERGY

[75] Inventor: Richard W. Lewis, Wilmington, Del.

[73] Assignee: E. I. Du Pont de Nemours and Company, Wilmington, Del.

[21] Appl. No.: 281,783

[22] Filed: Dec. 9, 1988

[51] Int. Cl.[4] ............................................ G01N 22/00
[52] U.S. Cl. .................................................... 324/636
[58] Field of Search ............... 324/58 C, 58.5 C, 58 R

[56] References Cited

U.S. PATENT DOCUMENTS 3,458,808  7/1969  Agdur ............................ 324/58.5 C

FOREIGN PATENT DOCUMENTS 1322131  5/1989  U.S.S.R. .......................... 324/58.5 C

OTHER PUBLICATIONS

Tiuri and Liimatainen, "A Microwave Method for Measurement of Fiber Orientation in Paper," *Journal of Microwave Power*, 10(2), 1975, pp. 141–145.

Bosisio et al., "The Regenerative . . . (RDT) . . . ," Conference; fourth *European Microwave Conference; Montreux, Switzerland* (10–13 Sep. 1974).

Joglekar et al., "A Rectangular Waveguide Orthomode Transducer;" Int. J. Electronics, vol. 47, No. 5, pp. 525–527, Nov. 1979.

*Primary Examiner*—Reinhard J. Eisenzopf
*Assistant Examiner*—Jack B. Harvey
*Attorney, Agent, or Firm*—Bernard, Rothwell & Brown

[57]  ABSTRACT

Measurement apparatus and method utilizing microwave energy. A symmetric microwave cavity is excited to oscillate in at least two identical resonant modes having substantially the same resonant frequencies but different field orientations relative to each other. A sample to be measured is caused to interact with the identical resonant modes and the difference in the frequencies of oscillation of the modes is determined in order to measure a property of the sample.

11 Claims, 4 Drawing Sheets

DUAL MODE CAVITY

FIG. 7 CAVITY SIZE VS FREQUENCY, DENIER & ACCURACY

| SIZE INCHES | FREQUENCY GHz | DENIER | ACCURACY +/- DENIER |
|---|---|---|---|
| 10 | 1 | $10^4 - 10^6$ | 10 - 100 |
| 5 | 2 | $10^3 - 10^5$ | 5 - 20 |
| 2.75 | 4 | $10^2 - 10^4$ | 2 - 10 |
| 2.00 | 6 | $10 - 10^3$ | 1 - 5 |
| 1.50 | 8 | 5 - 200 | 0.5 - 2 |
| 1.00 | 12 | 2 - 100 | 0.1 - 1 |

MEASUREMENT APPARATUS AND METHOD UTILIZING MULTIPLE RESONANT MODES OF MICROWAVE ENERGY

FIELD OF THE INVENTION

This invention relates to apparatus and methods for the measurement of various properties of materials, such as, for example, film thickness, fiber denier, molecular orientation, dielectric properties, moisture content and the like utilizing microwave energy. More specifically, the invention pertains to apparatus which utilizes one or more microwave cavities having multiple resonant modes, the relationship of which resonant modes is affected by certain properties of materials to be measured and to measurement methods utilizing multi-resonant mode microwave energy.

BACKGROUND OF THE INVENTION

In the production of filamentary and/or web materials such as, for example, films, papers and the like, it is important that any variations in certain properties of such materials be detected not only for purposes of detecting defects for quality control purposes and rejection of defective material but also for monitoring of properties on-line to effect control of manufacturing processes. Detection of any variations in the properties being monitored should be made as they occur and with minimum delay before large quantities of unacceptable material are produced. In order to be most effective, such detection should be made by means of continuous, on-line monitoring of the properties being measured.

The use of microwave devices is known in the art for the measurement of certain properties, such as thickness and dielectric anisotropy, in papers, films and similar materials. A device for measuring properties of a material by microwave resonance techniques is disclosed in U.S. Pat. No. 3,458,808—Agdur, which describes a microwave resonant cavity having at least two resonant frequency peaks and which is driven by an external microwave generator which sweeps a range of frequencies. A selected property of the test material, such as thickness or moisture content, is determined by measuring the time interval between resonant frequency peaks which is affected by changes in the property being measured. Other such devices driven by external sweep oscillators are known in the art. Such devices have a basic disadvantage in that they must sweep the range of frequencies in order to take each measurement and can thus make only one measurement for each sweep cycle. They therefore are unable to detect changes or defects which may be present, for example, in short lengths of moving materials such as moving web or filamentary materials or in small amounts of material on a moving web or belt where the time interval for detection may be too short relative to the time required for a complete sweep.

In a paper by M. Tiuri and P. Liimatainen entitled "A Microwave Method for Measurement of Fiber Orientation in Paper", published in the Journal of Microwave Power, 10(2), 1975, a method of measuring the dielectric anisotropy of paper is disclosed in which a dual resonant mode microwave cavity having orthogonally oriented resonant modes is used. To the extent that the dielectric constant of the paper is different in one direction than in another, the resonant frequency of one of the orthogonal modes will be affected to a greater degree than the other. The degree and direction of anisotropy of the dielectric constant and hence the fiber orientation of the paper is thus determined. However, the system was not used to measure the properties of the material nor was there any suggestion of any such possible use. Other methods of measuring magnetic or dielectric anisotropy at microwave frequencies have been suggested in the prior art.

In a paper entitled "Microwave Moisture Meters for the Paper and Pulp Industry" by Kjell Lindberg and Ulf Ternstrom, published in Measurement and Control, Vol. 3, March, 1970, various techniques are disclosed for measuring the moisture content of paper web using changes in the resonant frequency of a microwave cavity caused by the wet material. It is suggested in that paper that a resonator having an infinite number of discrete resonant frequencies, each belonging to a certain mode of oscillation and having a certain field configuration, can be utilized. It is further suggested that a measuring mode can be selected which has a field configuration such that the wet material affects the resonant frequency belonging to that mode significantly, and that a reference mode can be selected with a field configuration such that the resonant frequency is substantially independent of the wet material. There is no suggestion as to how this might be accomplished. Further, the suggestion does not deal with the type of cavity to be used and assumes that a discrete and different resonant frequency for each mode would be necessary.

Other means for measuring properties of materials include capacitive and infrared sensing devices and techniques. Capacitometers are sensitive to electrostatic charges which build up on certain materials such as yarn or film and which create sources of noise in the measurements. When used in a yarn line, most capacitometers have the electric field oriented perpendicular to the yarn line and thus can not be used for measurements on flat yarns because they yield different readings dependent on fiber orientation in the field. Infrared sensors for measuring certain properties such as moisture content are very slow and can require a number of yards of moving material to obtain a measurement, so that localized or short length variations are either averaged out or not detected at all.

SUMMARY OF THE INVENTION

The present invention provides apparatus and methods for rapidly measuring the properties of a material, which may be moving at a relatively high speed through the measurement means, which overcome the aforementioned disadvantages of the prior art apparatus and methods. The present invention comprises, in one embodiment thereof, apparatus incorporating a microwave cavity which supports identical resonant modes which are generated within the cavity and which are orthogonal to each other, and means for continuously monitoring a difference frequency between the resonant frequencies of the two orthogonal modes to detect and measure variations in the properties of a test material which is caused to interact with and thereby change the resonant frequency of one of the modes to a greater degree than the resonant frequency of the other mode. The use of identical resonant orthogonal modes permits optimizing the sensitivity of one mode to variations in the properties to be measured while the other mode may be configured to remain relatively insensitive to such variations. Where a selected property affects both modes, for example in the case of a web or a film, the degree of anisotropy can be measured by the difference in the two frequencies. Since changes in ambient temperature, moisture and other conditions have substantially identical effects on the normal resonant frequencies of the two identical modes, the difference frequency will remain relatively insensitive to such changes and the measurement accuracy is thereby enhanced. In addition, continuous monitoring of the difference frequency provides the capability of near instantaneous sensing of changes in the properties as they occur. The invention will be better understood and other advantages thereof apparent from the detailed description set forth below with reference to the accompanying drawings.

BRIEF DESCRIPTION OF THE DRAWINGS

FIG. 7 is a table listing certain measurement and accuracy data pertaining to the system of the invention;

DETAILED DESCRIPTION OF THE INVENTION

Figure 1:
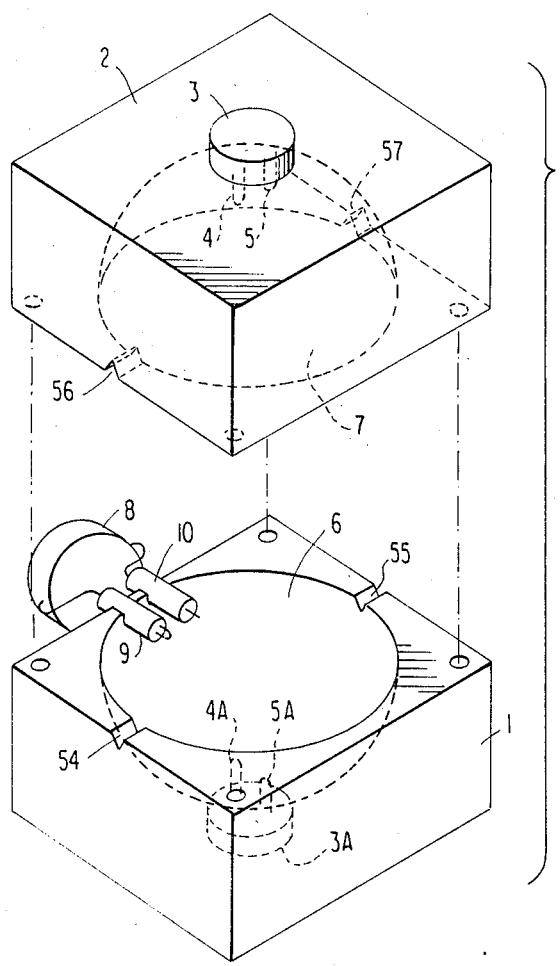
FIG. 1 is a perspective view of the major components of a measurement device embodying the present invention illustrated in a format to show the assembly thereof.

The embodiment of the invention illustrated in FIG. 1 comprises two main components 1 and 2 which, in assembled form, are secured together such as by bolts or pins when the two components are placed together along the alignment shown by the dotted lines. The components 1 and 2 contain hemispheric cavities 6 and 7 respectively which form a single spherical microwave cavity when the two components are assembled together. The microwave cavity formed by the hemispheric cavities 6 and 7 is preferably a single n-fold ($n \geq 2$) symmetric (such as a cube or a sphere), resonant mode cavity. One important property of such a cavity is that for a given microwave excitation frequency, the n-fold symmetric cavity can support at least n independent (uncoupled) sets of identical modes at n probe locations. Changes in ambient temperature, moisture and other conditions will therefore have the same effect on all modes and measurements of frequency differences caused by sample properties will therefore be substantially unaffected. Thus, while the microwave cavity shown in FIG. 1 is spherical in shape, it can be in the shape of a cube or in other form in accordance with the preferred embodiment of n-fold symmetry as described above.

The embodiment of FIG. 1 can be fabricated in a wide range of cavity sizes. The microwave frequency is determined by the diameter of the spherical cavity generally in accordance with the following formula:

Frequency (Ghz) = 10.3153/diameter(inches)

An amplifier 3 is mounted in a circular aperture in the top of component 2 as shown in FIG. 1. Extending from the amplifier 3 and into the cavity 7 are amplifier loops 4 and 5. A second amplifier 3A is mounted in the same fashion on the bottom of component 1 with loops 4A and 5A extending into the cavity 6.

The amplifier loops 4 and 5 are aligned and positioned at a 90° angle with respect to the alignment of the amplifier loops 4A and 5A. When power is applied to the amplifiers 3 and 3A, two identical but orthogonal fields having the same resonant frequency are generated in the spherical cavity formed by the joined hemispheric cavities 6 and 7. Since the two orthogonal fields are identical by reason of the symmetry of the cavity formed by the hemispheres 6 and 7, changes in ambient temperature, moisture and other conditions will have the same effects on the two fields, which effects will be subtracted out when the difference frequency is taken.

It should be noted that with the 90° orientation of the amplifiers 3 and 3A and their corresponding loops 4 and 5 and 4A and 5A, two identical resonant modes of continuous oscillation are excited in the cavity. As used herein, "identical modes" means that the two modes are identical each with reference to its own excitation loops and 4 and 5 and 4A and 5A respectively even though the modes are substantially orthogonal to each other when viewed from an external common reference. Thus, if one mode were selected as a $TM_{010}$ mode, then the other mode would be an identical $TM_{010}$ mode when viewed from the reference of its respective loop orientation. However, while the two modes are thus identical, they need not be exactly orthogonal for purposes of the invention. Changes from a precise orthogonal orientation will affect the relative sensitivities of the modes to measurement parameters but can be tolerated with a permissible range as long as the primary orientation is substantially orthogonal in the case of two identical modes.

Also extending into the microwave cavity at a position approximately at the joinder of the two hemispheric halves 6 and 7 are a loop sensor 9 and a probe sensor 10, which sense separately each frequency of the two orthogonal fields. The loop sensor 9 senses the magnetic field associated with the measurement frequency E-field and the probe sensor 10 senses the reference E-field. The two sensed frequencies are connected to an RF mixer 8 which produces a signal which is a function of the difference between the two sensed frequencies.

Figure 2A:
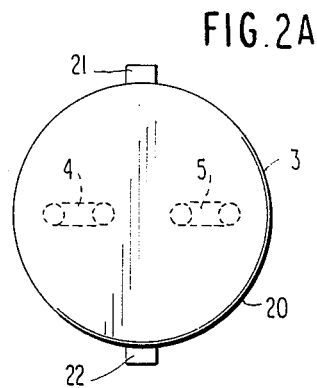
FIGS. 2A, 2B and 2C are top, bottom and side views respectively of an amplifier unit which is a component of the embodiment of FIG. 1.
Figure 2B:
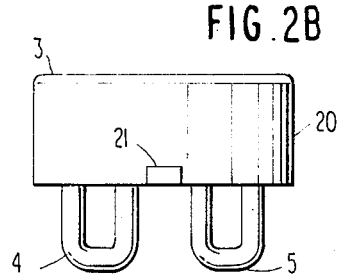
Figure 3:
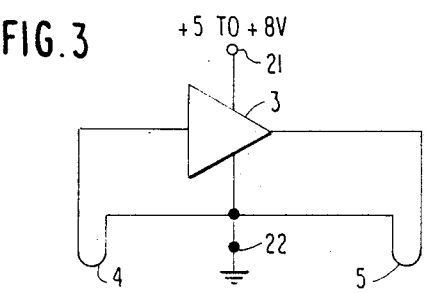
FIG. 3 is a partial circuit diagram of the amplifier unit of FIGS. 2A, 2B and 2C.
Figure 2C:
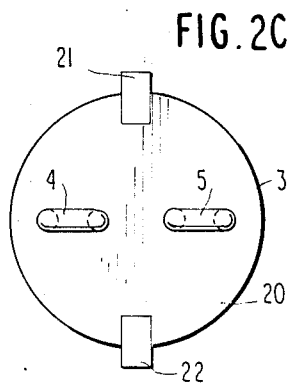

The amplifiers 3 and 3A are identical in construction as illustrated in FIGS. 2A–2C for amplifier 3. The components and circuitry of the amplifier 3 are enclosed in a container 20 and the loops 4 and 5 are mounted on the bottom thereof spaced apart and aligned with each other. Terminals 21 and 22 are provided for connection of the amplifier to a source of power. The circuit diagram of the amplifier 3 is shown in schematic form in FIG. 3. Amplifier 3A is of the same construction and both of the amplifiers 3 and 3A are self-contained and mounted integrally with the assembly of the elements 1 and 2 to form an integral assembly connectible to a power source and to suitable output instrumentation. The element 1 contains slots or grooves 54 and 55 on opposite sides of the cavity portion 6 to allow test samples to be suspended in the cavity or passed through the cavity in a continuous motion. Other means of introducing test samples into the cavity may be utilized and various other exemplary arrangements are shown and described in connection with other embodiments of the invention herein presented.

Figure 4:
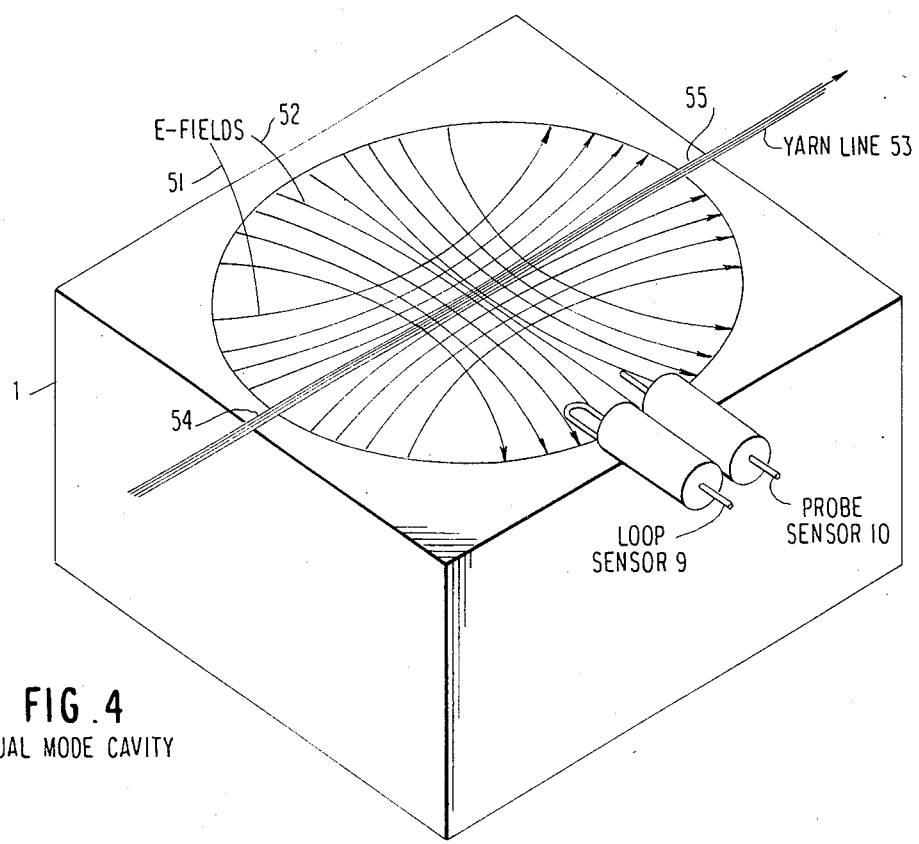
FIG. 4 is a perspective view of a portion of the device of FIG. 1 illustrating the field orientations thereof in relation to a test sample.

The two orthogonal fields generated by the amplifiers 3 and 3A when mounted in 90° orientation with respect to each other are illustrated schematically in FIG. 4 using the lower component 1 for purposes of illustration and wherein the E-field associated with the measurement frequency is shown by lines 51 and the E-field associated with the reference frequency is shown by lines 52. Also illustrated in FIG. 4 is a yarn line 53 which extends through the slots or grooves 54 and 55, 56 and 57 formed in opposite sides of the elements 1 and 2 to permit the yarn 53 to be drawn through the cavity at approximately the midpoint of the cavity formed by the two hemispheric sections 6 and 7 when assembled together to form the single microwave cavity.

As illustrated in FIG. 4, the yarn line 53 runs parallel to the measurement frequency E-field 51. Changes in the properties of the yarn 53, such as the complex dielectric constant and/or the mass, cause a shift in the resonant frequency of the measurement frequency E-field 51 without substantially affecting the resonant frequency of the reference E-field 52. The magnitude of the shift in the frequency of the measurement field is proportional to the magnitude of the changes in the properties being measured.

Figure 5:
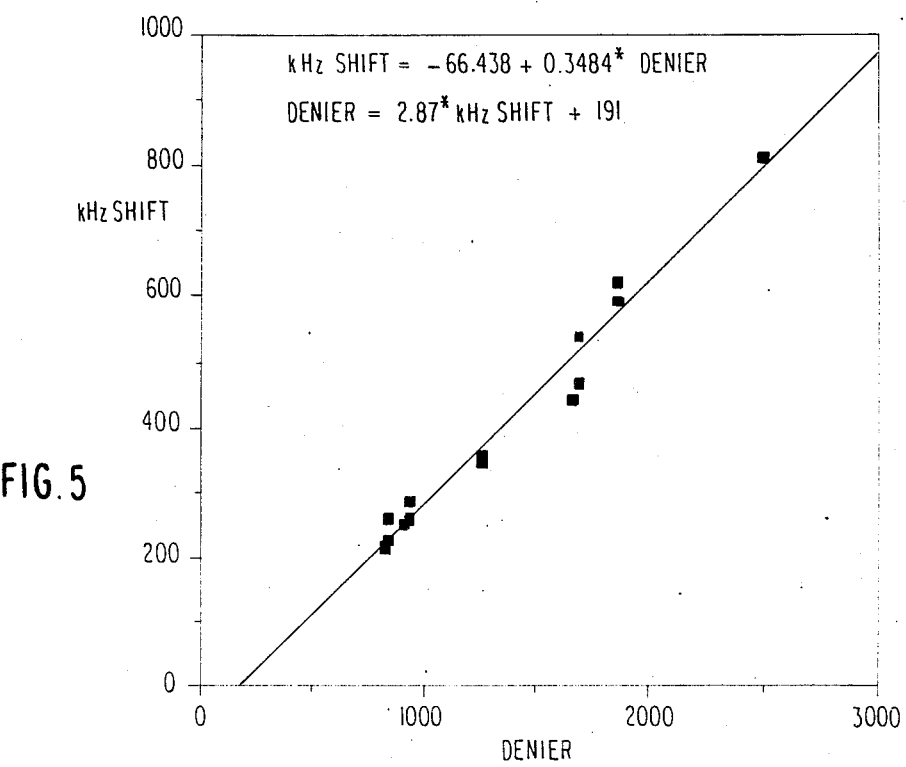
FIG. 5 is a graph presenting certain measurement data taken with the apparatus and method of the invention.

As mentioned above, the two microwave frequency signals are fed from sensors 9 and 10 into the RF mixer 8 which produces a frequency which is equal to the difference between the two frequencies. Data showing the frequency difference as a function of change in denier for Nylon fiber are shown in FIG. 5. It will be observed that the frequency is substantially linear with respect to change in denier.

Figure 6:
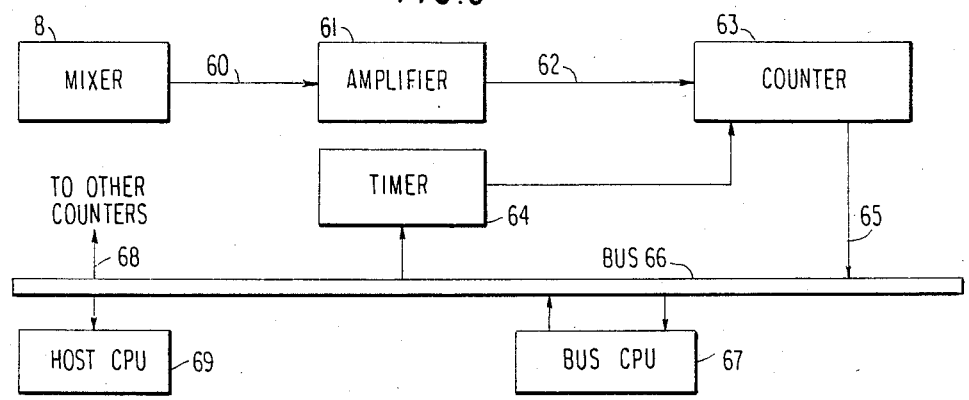
FIG. 6 is a block diagram of a system embodying the present invention.

The frequency output of the mixer 8, which is the difference frequency, is measured in one embodiment by means of a frequency counter as illustrated in the block diagram of FIG. 6. The output of the mixer 8, shown at 60, is connected to an amplifying pulse generator 61 which converts the difference frequency signal from a low level RF signal to a pulse train output at 62, which may be in the form of a TTL pulse output. The pulse train at 62 is connected to a counter 63 which is controlled by a timer 64 to count the number of pulses over a selected time interval, which is very short compared to the time variations of the properties being measured and which is preferably selected such that the measurement is virtually continuous and instantaneous with respect to the variables being measured and monitored. Many thousands of counts per second of the frequency difference signal can be measured with appropriate computer software. Generally, samples can be taken at rates inversely proportional to accuracy, for example 1,000 readings per second with a resolution of 1 KHz for the difference frequency reading.

In the embodiment shown in FIG. 6, the output of the counter 63, shown at 65, is fed to a main bus 66 which is in turn connected to a central processor unit 67 which monitors the signal and which can be connected to suitable control mechanisms to effect on-line control of the parameter being measured. The bus 66 can be connected to other counters through line 68 to monitor the outputs of other similar microwave cavity measurement systems and can also be connected to a host CPU 69 which monitors and controls the entire system of measurement and control.

The use of the n-fold symmetric resonant cavity with the identical but orthogonal modes provides very high accuracy of measurement over a range of conditions and variations in the parameters being measured. The table of FIG. 7 is a listing of typical data showing the general relationship of cavity size to sensor frequency, range of denier of test samples, and accuracy of measurement for spherical cavity sizes ranging from one to ten inches in diameter. The device was calibrated using materials of known denier.

Figure 8:
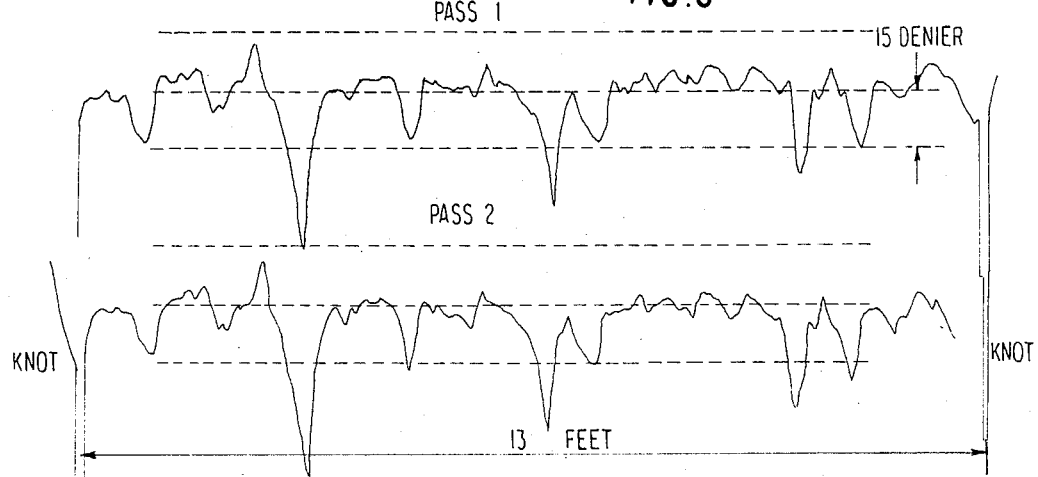
FIG. 8 is a graphical presentation of certain additional measurement data obtained with the system of the present invention.

FIG. 8 is a plot of denier variation measured in the laboratory for 380 denier aramid yarn for a thirteen foot length that was tied into a loop and continuously passed through a 2 GHz microwave device embodying the present invention. Measurements are shown for two passes and remained constant for large numbers of passes of yarn through the device.

Figure 9:
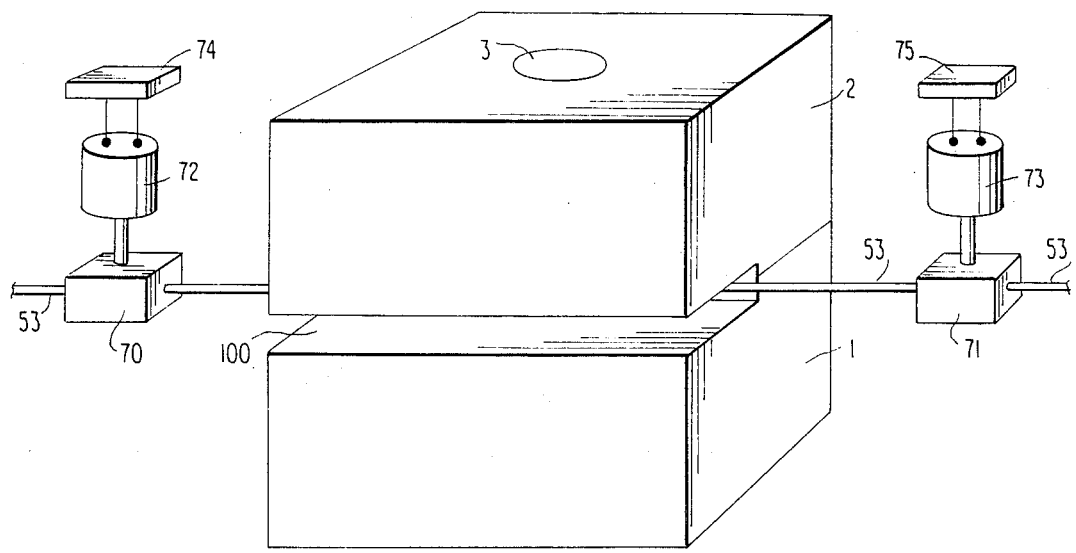
FIG. 9 is a perspective view of another embodiment of the invention.

FIG. 9 is a perspective view of another embodiment of the invention in which the elements 1 and 2 are connected together and in which a slot 100 is formed to extend approximately halfway through the device to permit the yarn line 53 to travel through the center of the cavity and be threaded up on the fly. This allows convenience of threading in a production operation without breaking the continuity of the yarn line because yarn can be threaded from the side through slot 100. Amplifier 3 is shown mounted on the top of the device and amplifier 3A, not visible in the illustration of FIG. 9, is mounted on the bottom side as illustrated in FIG. 1 with the two amplifiers oriented at a 90° angle with respect to each other to generate the orthogonal fields. The yarn 53 is moved through the slot 100 by drive means 70 and 71 and motors 72 and 73 which are controlled by control means 74 and 75 to maintain proper tension on the yarn 53. Continuous monitoring of selected properties of the yarn is achieved by sensing the difference in the frequencies of oscillation of the orthogonal modes.

Figure 10:
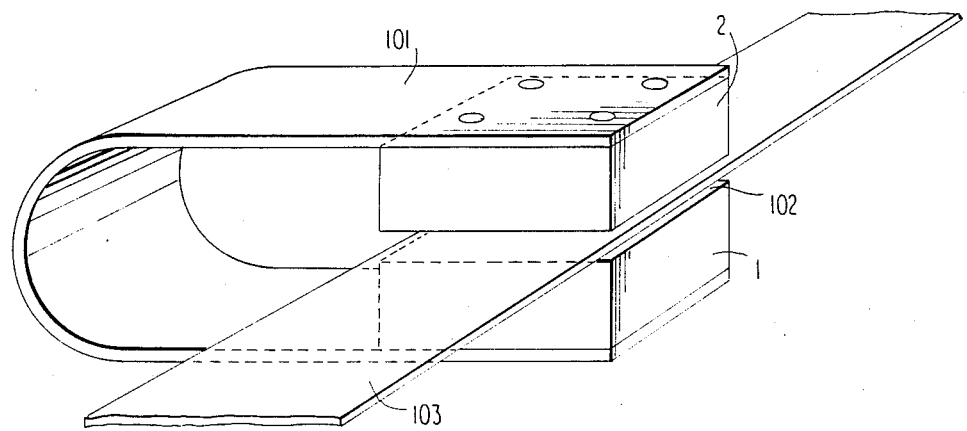
FIG. 10 is a perspective view of still another embodiment of the invention for web or film measurement.

FIG. 10 shows still another embodiment in which the elements 1 and 2 are mounted on a bracket 101 to form a slot 102 extending entirely through the device to permit a sheet of material 103 to pass entirely through the sensor cavity. The sheet of material 103 can be moved continuously through the slot 102 in any suitable manner such as by drive and control means as illustrated in FIG. 9. The bracket 101 should be rigid to hold the distance of separation of the elements 1 and 2 constant and to resist vibration. The distance of separation between the two elements 1 and 2 should preferably be less than about 3% to 4% of the cavity diameter.

In the case of a film or a web such as in form of a sheet material 103 as shown in FIG. 10, if a selected property is isotropic it will have the same effect on the resonant frequencies of both fields and, while both resonant frequencies will thus change, no difference in the resulting resonant frequencies will be measured if the parameter is completely isotropic. In such systems, the invention can be used to measure the degree of isotropy or anisotropy in selected properties in a film or web.

Since both of the identical modes are in continuous oscillation, the difference in frequency between the two modes can be measured substantially continuously and readings taken many thousands of times per second with practical instrumentation techniques. Thus even very small defects, such as for example a knot in a yarn line, can be detected at very high line speeds such three thousand yards per minute or so in a yarn line.

Because the identical modes are caused to oscillate continuously in the same cavity at substantially the same frequencies, the effects of changes in ambient conditions and similar perturbations will be substantially identical for the two modes, thus causing no substantial change in the difference frequency between the modes and permitting measurements of very high accuracy to be made.

In the case of a web or film as illustrated in FIG. 10, one field may be oriented parallel to the plane of the web and the second field perpendicular to the web. This permits measurement of the thickness of the web using the difference frequency in the manner described above. Various other field orientations to measure selected properties can be utilized with the present invention.

Although spherical cavities are preferred, other cavities geometries such as cubic and cylindrical can also be used in accordance with the teachings set forth above. Various other modifications and substitutions in and to the embodiments presented herein and falling within the true scope and spirit of the appended claims will occur to those skilled in the art and it should be understood that the embodiments presented herein are set forth for purposes of full and complete disclosure of the invention and are not intended as limiting in any way.

What is claimed is:

1. Measurement apparatus utilizing microwave energy comprising:
   a. an n-fold symmetric self-oscillating microwave cavity (where n is an integer equal to or greater than 2) having at least two identical resonant modes of oscillation at substantially the same frequency, each with a different field orientation;
   b. means for exciting said cavity to oscillate simultaneously and continuously in each of said at least two identical resonant modes at substantially the same frequency;
   c. positioning means for positioning a sample of material to interact with said at least two identical resonant modes so that a property of said sample which is to be measured changes the resonant frequency of oscillation of at least one of said resonant modes from its normal resonant frequency; and
   d. means for measuring the difference in the simultaneously and continuously excited resonant frequencies of oscillation of said at least two identical resonant modes with said sample so positioned to measure said property of said sample.

2. Measurement apparatus as set forth in claim 1 in which the E-fields of said at least two identical resonant modes of oscillation are substantially orthogonal to each other.

3. Measurement apparatus as set forth in claim 1 in which said positioning means includes means defining a path of movement for said sample through at least a portion of said microwave cavity.

4. Measurement apparatus as set forth in claim 1 in which said means for measuring the difference in frequencies includes means for producing an output signal which varies in frequency as a function of said difference in frequencies.

5. Measurement apparatus as set forth in claim 1 in which said means for measuring the difference in frequencies includes means for producing an output signal which substantially continuously and instantaneously responds to said difference in frequencies.

6. Measurement apparatus as set forth in claim 4 including means for converting said output signal into a pulse train the pulse rate of which is proportional to the frequency of said output signal.

7. Measurement apparatus as set forth in claim 6 including means for counting the number of pulses in said pulse train in a selected time interval as a means of determining the frequency of said output signal.

8. Measurement apparatus as set forth in claim 1 in which said means for exciting said cavity is integrally incorporated in said apparatus adjacent to said cavity and with portions thereof extending into said cavity.

9. Measurement apparatus as set forth in claim 8 in which said means for exciting said cavity includes two amplifiers positioned adjacent to different portions of said cavity with each of said amplifiers having loops extending into said cavity and being oriented to excite simultaneous and continuous identical resonant modes of oscillation which are substantially orthogonal to each other.

10. A measurement method utilizing microwave energy comprising:
    a. exciting in an n-fold symmetric self-oscillating microwave cavity (where n is an integer equal to or greater than 2) in at least two identical resonant modes of simultaneous continuous microwave oscillation at substantially the same resonant frequencies;
    b. positioning a sample of material to interact with said at least two identical resonant modes to cause a property of said sample to be measured to change the resonant frequency of oscillation of at least one of said simultaneous and continuous oscillation resonant modes from its normal resonant frequency; and
    c. measuring the difference in the frequencies of oscillation of said at least two identical simultaneous and continuous oscillation resonant modes while so positioning said sample to measure said property of said sample.

11. The method of claim 10 in which the E-fields of said at least two identical simultaneous and continuous oscillation resonant modes are positioned substantially orthogonal to each other.

* * * * *